US008758021B2

(12) United States Patent
Takahashi (10) Patent No.: US 8,758,021 B2
(45) Date of Patent: Jun. 24, 2014

(54) REMOTE INTERNET TECHNICAL GUIDANCE/EDUCATION DISTRIBUTION SYSTEM USING PRACTITIONER'S VISION, AND GUIDANCE SYSTEM USING COMMUNICATION NETWORK

(76) Inventor: Atsushi Takahashi, Fukui (JP)

( * ) Notice: Subject to any disclaimer, the term of this patent is extended or adjusted under 35 U.S.C. 154(b) by 1737 days.

(21) Appl. No.: 10/250,424

(22) PCT Filed: Dec. 26, 2001

(86) PCT No.: PCT/JP01/11444
§ 371 (c)(1),
(2), (4) Date: Nov. 25, 2003

(87) PCT Pub. No.: WO02/054309
PCT Pub. Date: Nov. 7, 2002

(65) Prior Publication Data
US 2004/0072134 A1    Apr. 15, 2004

(30) Foreign Application Priority Data
Dec. 28, 2000 (JP) ................................ 2000-403305

(51) Int. Cl.
G09B 23/28 (2006.01)
(52) U.S. Cl.
USPC ........... 434/262; 434/350; 434/353; 434/118; 348/43; 348/77; 348/108; 348/345
(58) Field of Classification Search
CPC ....................................................... G09B 23/28
USPC ................. 434/118, 322, 323, 350, 353, 362; 348/43, 77, 108, 345
See application file for complete search history.

(56) References Cited

U.S. PATENT DOCUMENTS

| 4,199,785 | A | * | 4/1980 | McCullough et al. | 348/704 |
|---|---|---|---|---|---|
| 4,392,726 | A | * | 7/1983 | Kimura | 348/355 |
| 4,395,731 | A | * | 7/1983 | Schoolman | 348/53 |
| 4,516,157 | A | * | 5/1985 | Campbell | 348/158 |
| 4,616,257 | A | * | 10/1986 | Kloots et al. | 348/370 |
| 4,621,283 | A | * | 11/1986 | Feinbloom | 348/77 |
| 4,636,866 | A | * | 1/1987 | Hattori | |
| 4,706,117 | A | * | 11/1987 | Schoolman | 348/53 |
| 4,786,966 | A | * | 11/1988 | Hanson et al. | 348/158 |
| 4,933,755 | A | * | 6/1990 | Dahl et al. | 348/53 |
| 4,982,278 | A | * | 1/1991 | Dahl et al. | 348/53 |
| 5,048,077 | A | * | 9/1991 | Wells et al. | 379/93.17 |
| 5,493,595 | A | * | 2/1996 | Schoolman | 378/41 |

(Continued)

Primary Examiner — Sam Yao
Assistant Examiner — Alvin Carlos (57) ABSTRACT

There is disclosed a system of providing technical guidance and instruction by utilizing two zoom lens equipped auto focus CCD cameras placed directly in front of the instructor's left and right pupils and communication networks, such as internet. More specifically, a business system is disclosed which distributes technical guidance and instruction on medical surgeries and other highly precision oriented technical work performed in person, and/or an education guidance system which a specific client performs a medical surgery or other highly precise and technical work. In addition, the business system will have the capability of settling tuition/instruction fees which arise from providing the technical guidance and instructions, recruiting potential students, and settlement of payments to the instructors.

6 Claims, 7 Drawing Sheets

(56) References Cited

U.S. PATENT DOCUMENTS

| | | | |
|---|---|---|---|
| 5,515,268 A * | 5/1996 | Yoda | 705/26 |
| 5,677,728 A * | 10/1997 | Schoolman | 348/14.15 |
| 5,905,525 A * | 5/1999 | Ishibashi et al. | 348/39 |
| 5,917,460 A * | 6/1999 | Kodama | 345/8 |
| 5,991,085 A * | 11/1999 | Rallison et al. | 359/630 |
| 6,201,394 B1 * | 3/2001 | Danby et al. | 324/319 |
| 6,266,642 B1 * | 7/2001 | Franz et al. | 704/277 |
| 6,347,333 B2 * | 2/2002 | Eisendrath et al. | 709/217 |
| 6,414,708 B1 * | 7/2002 | Carmeli et al. | 348/42 |
| 6,847,336 B1 * | 1/2005 | Lemelson et al. | 345/8 |

* cited by examiner

REMOTE INTERNET TECHNICAL GUIDANCE/EDUCATION DISTRIBUTION SYSTEM USING PRACTITIONER'S VISION, AND GUIDANCE SYSTEM USING COMMUNICATION NETWORK

FILED OF THE INVENTION

This invention relates to a system of providing technical guidances and instructions by utilizing communication networks such as the internet. More specifically, this invention provides a business system which distributes technical guidance and instruction on medical surgeries and other highly precision oriented technical work performed in person, and/or an education guidance system (a lay person presumed to be a robot is controlled from a remote location through vocal and visual instruction through the use of information collected from the range of vision and view point of the person presumed to be a robot) which a specific client performs a medical surgery or other highly precise and technical work. In addition, this invention provides a business system with the capability of settling tuition/instruction fees which arise from providing the technical guidance and instructions, recruiting potential students, and settlement of payments to the instructors.

DESCRIPTION OF THE PRIOR ART

Generally, in an instructional or educational program or class to provide live viewing of medical surgery or highly technical precision oriented work, and especially to provide viewing from the most ideal viewpoint, similar or identical to the viewpoint of the instructor, it was very time consuming for each student to take turns at observing the work performed and it was also inevitable to have physical limitations due to the size of the facility to limit the number of students (clients) who would be able to attend and view the work simultaneously. For these reasons, the number of students were limited to small number. In addition, when the instructional technician (instructor) and the students (clients) spoke different languages, the cost of tuition per student became very high because a simultaneous translator had to be present at the scene.

When medical surgery is performed, it is usually very difficult to transport the patient to a distant location, and for other technical work demonstration, if it required a large scale equipment or facility, or if it involves equipment which could not be easily moved, the students (client) had to adjust their schedule and spend a lot of time and money for travel to be at the location. In addition a student with an interest to attend a live instruction had to rely solely on the advertisement placed by the instructor or to rely on a subjective view of an acquaintance who had attended a session by the instructor to evaluate the value of the program and decide to whether attend a program or not. The payment method for the program had to be made according to the specified method by the instructor. On the other hand, the instructor hosting the guidance or education program had to utilize various advertisement medium to place advertisement, and regardless of the number of the students attending the program, once an application was received from the student, the instructor still had to confirm the receipt and collection of the tuition.

On the other hand, when the technical or precision work demonstration or the medical surgery is performed at a distant/remote location, the instructor must travel to the location, and it required considerable amount of travel expenses. In addition to the expenses, the extensive time required to travel to the remote location also made it extremely difficult to deal appropriately with an emergency operation. If the surgery also required more than one instructor to participate, the amount of the travel expense rose higher and also became exceedingly difficult to deal appropriately with an emergency operation. When the student and the instructor spoke different languages, it was also necessary to have an interpreter travel with the instructor to the location, adding more expenses.

Due to the legal regulation of medical licensing which prohibits medical treatment in foreign countries, generally the instructor would not be able to directly operate on a patient outside of the instructor's native country, therefore not allowing an instructor to hold a instructional/educational program on surgery when it involved a live demonstration of the instructor directly operating on a patient.

In addition, when students request instructions and guidance for medical surgery or other precision oriented special technical work, the selection of the instructor was inevitably limited to person known to the group of students, and there were no specific standard for calculating the cost or the fee to be paid to the individual instructor, therefore required direct negotiation with the instructor, causing not only extra hardship in selecting an instructor, but also made complicated the administrative process of calculating the appropriate fee from the time length of the program, contents of the program and paying the appropriate amount to the instructor.

SUMMARY OF THE INVENTION

The present invention provides a solution to one of problems as follows. Considering the situation explained above, when an instructor operates or starts an educational or instructional program on medical surgery or precision oriented special technical work which involves direct observation of a live work performed by the instructor, this invention allows, even when the surgery is done to a closed area of body, to have numerous students to observe the live work from the best possible view point, with live commentary by the instructor and observation of the surrounding environment of the work being performed, thus creating a condition as if the student is at the location observing the actual work, at a comparatively lower cost.

When the work performed is a medical surgery, this invention allows the instructor to operate on a patient without having the patient travel to the facility where the students could observe the surgery and if the nation issuing the medical license to the instructor is different from the one of the students, the instructor would be allowed to provide instructions across the national borders to the students without the limitation of the medical licensing law.

In addition, even when the spoken language different between the students and instructor, there will no longer be a need for an interpreter to travel to the location of the program. When the location of the work is within the national boundary, there will be no need for the students to travel to the location where the work is performed, saving on travel time and expenses.

This invention also allows to simplify the administrative process of settling tuition payments and also allows an objective standard in setting instructors ranking or evaluation, compared to the previous situation when students had to rely solely on advertisements placed by the instructors and on subjective view of their peers or acquaintances who has taken the specific instructor's program.

In addition, this invention creates a business model which provides an efficient method of advertisement of the program, and regardless of the number of students attending the program, the administrative process for receiving tuition payments from the student instructor can be completed at once.

When a student in a remote location desires to enroll in the educational program, despite the fact that it seems as if the one or more instructors demonstrating the work is right where the student is, there is no actual need for the instructor(s) to travel to the location of where the student is located, and as a result saves tremendous amount of travel cost and time, and if the work consists of medical surgery, this invention allows to deal with any emergency situation.

When the language spoken by the instructor and the student is different, it is no longer necessary to have an interpreter travel to the location, and allow savings in cost associated with the travel to be reduced.

In addition, when a client desires to purchase an educational program, the student no longer needs to rely solely on the advertisement placed by the instructor or to the subjective view of an acquaintance or a peer who had attended the program organized by the particular instructor. This invention allows the student to select an appropriate instructor from a wide range of instructors from a worldwide pool of specialists, and allows a clear pricing standard for each program offered by each instructor and to base the selection of instructor accordingly.

This invention also allows the simplification of the administrative process of paying for and accounting for the tuition payments made by the students and by the teacher, respectively.

Through utilizing the internet as a communication medium, this invention provides a distribution system of medical surgery or highly precision oriented technical work performed under the direct observation of the instructor, which an eyeglass type monitor comprising two auto focus zoom lens equipped CCD cameras placed directly in front of the instructor's pupils and a two- or three-dimensional digital magnification mirror type monitor screen where the image from the cameras is projected, is worn over the head of the instructor performing the surgery or the work, and the same image projected on the monitor which is the viewpoint of the instructor, is forwarded to the educational program distributor's server via the internet by utilizing the electronic terminal attached to the eyeglass type monitor, and the educational program distributor utilizing the server and internet is enabled to distribute and allow access to the virtual surgery experience program and/or virtual experience educational program of highly precision oriented technical work program by specific subscribers of the program by using identification numbers and password managed by specific subscribers to the program, allowing numerous number of subscribers to access to the program broadcasted live or as recorded program from the educational program distribution server for a fee.

The two zoom lens equipped auto focus CCD cameras placed directly in front of the instructor's left and right pupils representing the viewpoint of the instructor and the output of the image generated from the two dimensional or three dimensional image projected onto the digital magnification mirror, a cursor pointer, line image, arrow and other entries, and specific instruction and commentary from the instructor may be super imposed to the image and distributed.

When the distributed image is of a medical surgery, the information such as the patient's vital signs, temperature of the surgical equipment used, rpm of the surgical equipment used or the output level of the laser used, or the distributed image is of a highly precision oriented technical work, such information as the numerical figures for the amount of light, temperature, speed, pressure, humidity of the facility or the graphical image of these information may be distributed or broadcasted with the above referenced image of the work performed. In addition to distributing these images and information to the specific subscribers to the program via the internet as live broadcast or pre-recorded broadcast, a microphone may also be worn by the instructor performing the work, allowing a broadcast of education program which includes live commentary and description of the work performed by the instructor. If the language used by the instructor is different from the one used by the subscriber to the program, the educational program distributor's server may provide the translation from the language used by the instructor to the language used by the subscriber and broadcast in the language used by the subscriber. In addition, by using the internet, the education distribution server may receive questions from the subscriber and by utilizing the earphone worn by the instructor, questions and answers may be exchanged between the instructor and the subscriber.

As described above, by creating a business system which allows simultaneous broadcast of programs to numerous subscribers for fee, it creates a feeling of actually being at the site where the work or the surgery is performed when compared to pre-recorded and edited program, and even if the surgery is to a closed section of a body, it allows the subscriber to observe the surgery from the same ideal viewpoint of the instructor, and not just one step at a time but as one entire process. Therefore not only it allows numerous subscribers to observe the program simultaneously, it also allows to provide a high quality educational or instructional program at a lower cost. Even if the language used by the subscriber and the instructor are different, it allows translation of questions received by the educational program distributor's server to translate as it receives the question or to translate simultaneously and forward the question to the instructor. On the other hand, the oral instructions provided by the instructor while performing the work may be translated as it received or simultaneously by the educational program distributor's server into the language used by the subscribers for fee, it eliminates the need of sending a interpreter to the site. It also eliminates the need of transporting a patient from one medical facility to another for an educational program and also allows the instructor to provide these programs beyond the national boundaries without being limited by the regulation of medical licensing regulation of each country where the subscriber is located. Even when the instruction is provided and subscribed within the same country, the need for the subscriber to travel to the actual site of the performance is eliminated, lowering the cost and time involved for traveling and allow dealing with emergency situation at remote location.

In addition, in order to carry out this instructional program, the instructional program distribution company would have to provide on home page, the resume (career history) of the instructor, description of the technology or the specialty area of the program, language used, length of the program, fee, and other information for each program as general information for advertisement purpose and to also provide on a real time bases the popularity of the program and evaluation of the instructor by the subscriber could also be included. By providing these information, when subscriber may make an informed decision based on an objective information and data, to whether purchase a specific program or not, rather than solely basing the decision on a subjective view of an acquaintance who has purchased the program before or based solely on the advertisement placed by the instructor.

The program also allows the process of applying and paying for the program over the internet using the educational program distributor's home page. By allowing online processing, it relieves the subscriber from the complicated administrative process of applying and paying for the service, and also allows the instructors providing the program to understand and provide for the specific needs of the subscribers, lower the cost of advertisements, and relieves the instructor from the administrative process of collecting and accounting for the payment of fees paid by the subscriber for the program.

On the other hand, when the client at a remote location is to perform a medical surgery or other highly precision oriented technical work, the above mentioned system may be utilized in the reverse direction, via the internet, the image from the viewpoint of the client, and if the it is a medical surgery the vital signs of the client and other data of the surgery superimposed on the image and if the work involved highly precision oriented technical work, providing the amount of light, temperature, pressure, speed and other information of the equipment and facility as numerical figure or as a graph, to the instructor through the server of the educational program distribution company's server to one or more instructors at a remote location received by the instructor through their electronic device, and utilizing the microphone worn by the client, receive questions orally from the client, and utilizing the earphone worn by the client, provide oral instruction and through the eyeglass type monitor worn by the client, provide visual instruction using cursors and other markers, and provide educational and instructional service against actual work performed by the client, and lower or eliminate the time and cost for the one or more instructors to travel to the location, and to also deal with emergency situation.

When the language used by the client is different from the one used by the instructor, the questions received via the internet through the server of the educational program distribution company may be simultaneously or in order translated into the language of the instructor and forwarded to the client, and on the other hand, translate simultaneously or in order, the oral instruction from the instructor to the language of the client and forward to the client, as a two way communicable instructional educational program, provided to specific clients contracting to the service for a fee, and by eliminating the need of sending a translator to the site, enabling the cost of the program to be lowered significantly.

In addition, when a client is to purchase an individualized educational instructional program provided by several specialists of different field of expertise, the internet home page/web site of the educational program distribution company can provide a system where client may request a specific instructor to provide instructions, and by utilizing the home page/web site of the educational program distribution company, the instructor's area of expertise, details of the technology, language used, length of program and other information, and cost for individualized instructions/programs may be made available to the clients, avoiding the client to rely on advertisement placed by the instructor or on a subjective view of an acquaintance of the client who has subscribed or received instructions for the specific instructor, but instead make decisions based on an objective evaluation and also allow in the reverse to have the client request a specific instructor to provide the program. In addition the cost/fee for each instructor is clearly provided, it eliminates the negotiation it would otherwise be required. Since the instructors would be introduced on the home page/web page of the educational program distribution company's web page as a team of expertise for each specific field, it also allows a high level of specified and expert instructions. For medical surgery and for other highly precision oriented technical work are to be charged based on an unit for each specific type of technique involved or on a time unit basis which client may settle the payment over the educational program distributor's home page through the internet, which eliminates the need for clients to pay/settle fees due on an individual method, allowing to simplify the administrative procedure for settling accounts. In addition, for instruction on medical surgery and other highly precision oriented technical work, where the amount of fee is determined on the unit of work based on the type of technical work performed or on the unit of work based on time, the cost for receiving the instruction may be settled via the internet on the home page/web page of the educational program distribution company, which would allow the instructor to receive automatically the appropriate amount of compensation based on the number of clients subscribing to the particular program, eliminating the need of complicated accounting procedure and relieving the instructor from administrative work.

This invention may also be organized in the following manner. Namely an eye glass type monitor worn on the head of an student (one receiving the instruction), and a cameras placed close to the monitor and placed toward the vision of the student, and the image taken by this cameras and the data of the image being outputted onto the eyeglass type monitor, and the method of relaying (broadcasting) the data of the image corresponding to the image reflected on the aforementioned monitor using internet or other communication network, and from the relaying the image, a distribution method to output the image onto monitor(s) attached to one or more devices which are attached to the communication network, and the guidance data from the instructor who reviews/observes the images on the aforementioned distribution monitor which is in reverse sent via the communication network back to the aforementioned eye glass type monitor, a guidance/instructional system which utilizes the above referenced communication network and the method to send data in reverse.

In the above described invention which includes, for the student and for the instructor, aforementioned eye glass type monitor, cameras, and microphone or other device to collect voice data, and a relay method to transfer not only the data of image but also the data of the voice collected, and utilizing the communication network, forwards/transfers the data to aforementioned devices #1 or #2, and outputted utilizing from the a specified location, such as a speaker, which in all is a guidance system that utilizes the communication network.

DETAILED DESCRIPTION OF THE PREFERRED EMBODIMENTS

Figure 1:
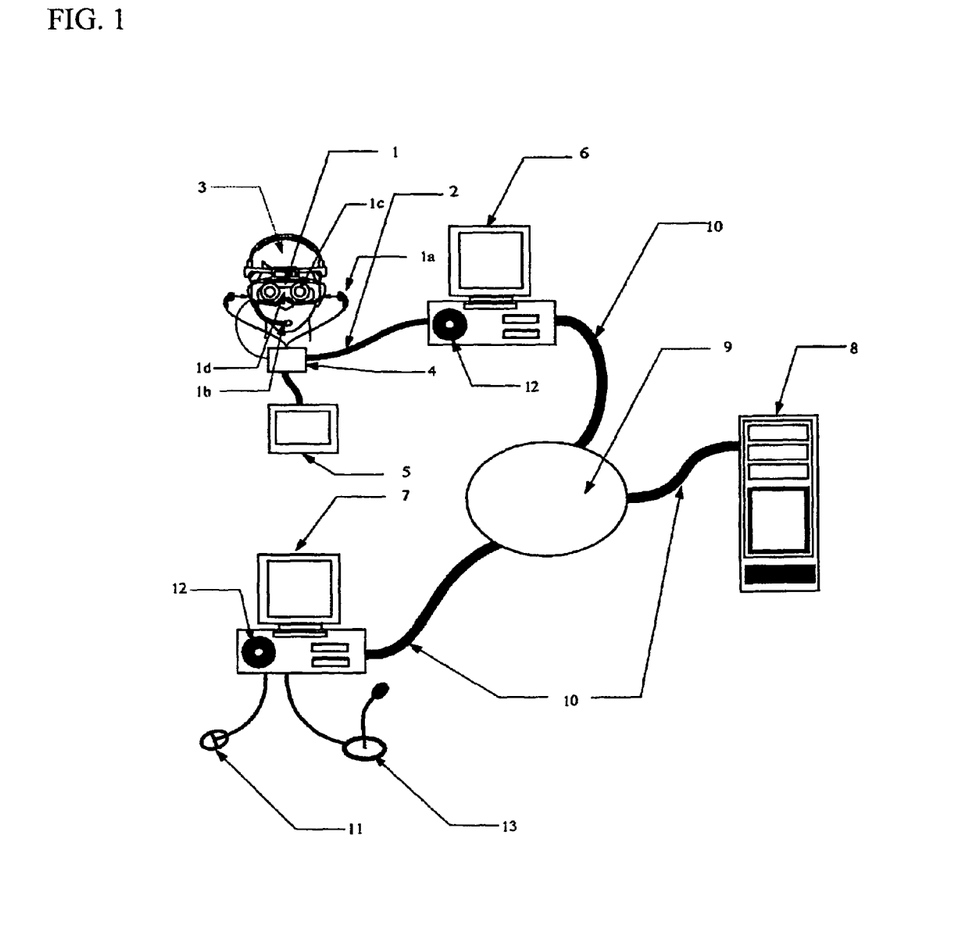
FIG. 1 is an overview/general organization of the technical guidance/instruction education distribution system.

FIG. 1 shows the basic model of the hardware for carrying out the educational program business model utilizing the internet. Throughout the drawings, whenever same term is used to indicate/describe the Fig., it is referring to the same part. The characteristic of the examples depicted in the Figs., as shown in FIG. 1, is the digital magnification mirror device which contains an eye glass type monitor worn on the head of the technician 1d and two automatic focus three dimensional CCD cameras 1c placed in front section of the eye glass type monitor with the cameras located in front of each pupil of the technician's eyes.

The image data A obtained from the digital magnification mirror device, and in medical surgery, the vital signs of the patient operated which is superimposed on the image data, and in highly precision oriented technical work, the condition of the equipment and facility used in the work and the surrounding environmental condition, such as amount of light, temperature, humidity, pressure and speed as numerical figure or as a graph, image data B, and the voice data C obtained from the microphone worn by the technician, and visual instructional data D, such as cursor pointer, lines, arrows and other markers written into the as instructional pointers, are sent from the personal computer device 6 which is attached to the internet 9, to the educational program distribution company's server 8.

The information received by the server 8 of the educational program distribution company is directly distributed to the personal computers 7 or the educational program distribution company's server 8 is to process the data by translating the data into different languages or to edit the image data. In the same manner, the personal computer 6 and the microphone on the personal computer 1b and the voice data C obtained from the microphone and the instructional pointers such as cursor pointers, lines, arrows and other pointers written in using the mouse as visual instructional data D may be sent to from the personal computer 6 connected to the internet 9 to the educational program distribution company's server 8.

The information received by the educational program distribution company's server 8, via the internet 9, may be directly sent to the personal computer 7, or may first be translated into different languages and/or the images edited, then sent to the personal computer 7.

Figure 2:
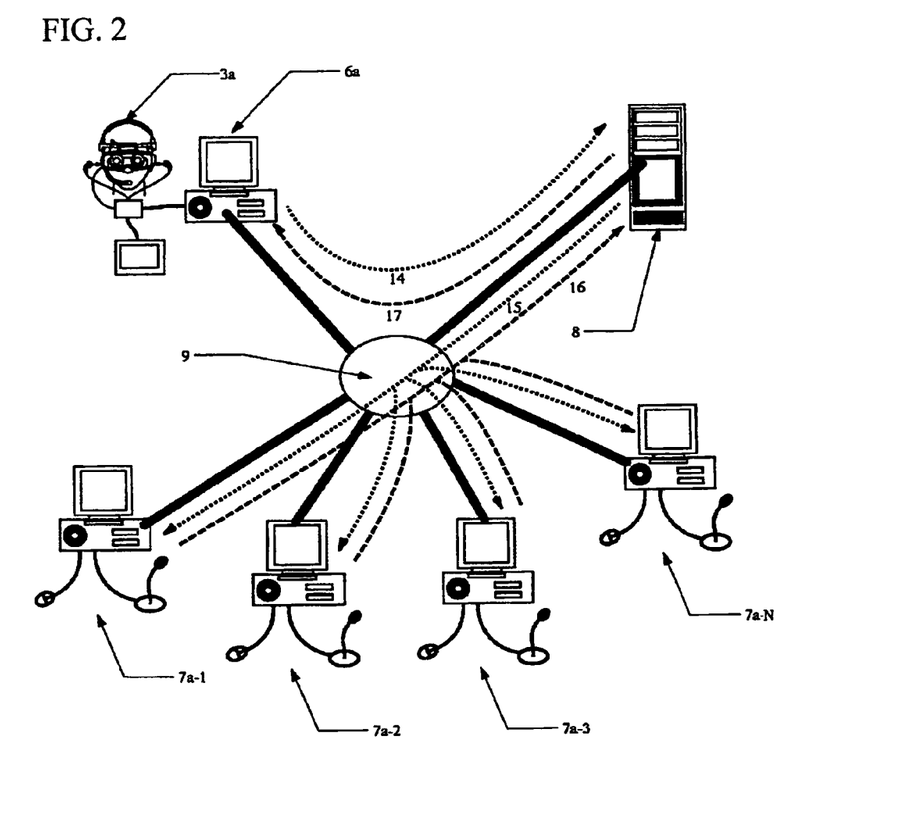
FIG. 2 is a system diagram of a technical guidance/instruction education distribution system which a technician is the instructor.
Figure 3:
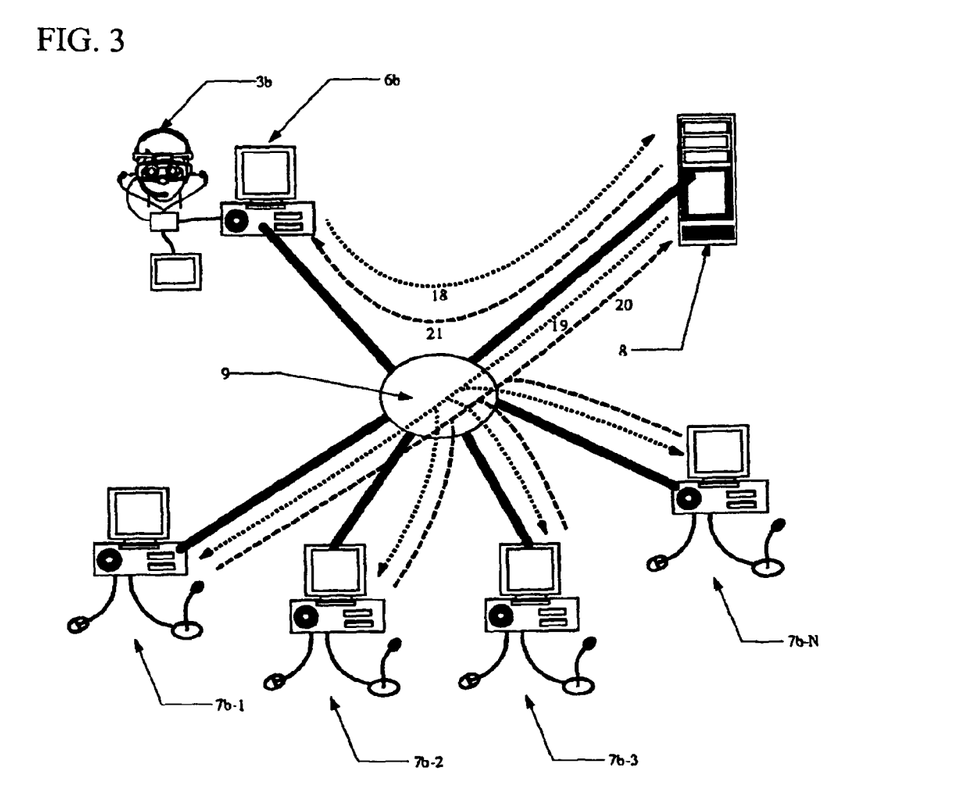
FIG. 3 is a system diagram of a technical guidance/instruction education system which a technician is the student (recipient of the instruction).

Next, within the distribution system shown in FIG. 1 and referred above, the method of providing instruction is explained in two separate implementation methods, as shown in FIG. 2 which the technician as the instructor provides instruction to students, and in the alternate as shown in FIG. 3 which the technician (student) receives instruction from the instructor.

As shown in FIG. 2, which the instructor 3a provides the educational guidance program of medical surgery or other highly precision oriented technical work which is performed in person under the direct observation of the instructor, the technician (instructor) wears the digital magnification mirror 1 shown in FIG. 1 and the enlarged viewpoint image obtained from the two dimensional or three dimensional CCD, which against this image, the data obtained from the vital monitor 5 or precision technique facility/equipment/environment monitoring device, through the utilization of the precision technique facility/equipment/environment, image, voice and vital sign editing input device, edited/composed by the personal computer 6a, and superimposed onto the image projected by the eye glass type LCD monitor 1d worn over the head of the instructor.

Above described image data projected on the LCD monitor 1d and the voice instructional data from the microphone 1b are through the internet 9 sent to the technical guidance educational distribution system distribution company's server 8 from the personal computer 6a. The data sent to the technical guidance educational distribution system distribution company's server 8, is simultaneously translated or translated in the order received if the language used by the instructor and the student is different, and sent to the student. It allows numerous contracting/subscribing students to receive this data on the personal computers 7a-1~7a-N and experience the medical surgery or other highly precision oriented technical work, and the surrounding environment, creating an virtual experience as if the student is at the actual location where the work is performed.

The above mentioned communication network may be used for transfer of information from both directions, therefore when a question from a student, by inputting the data by voice through the microphone 13 attached to the personal computer 7a-1~7a-N, the question/data via the internet 9 be sent to the technical guidance educational distribution system distribution company's server 8. When the language used by the student and the instructor is different, the data transferred may be simultaneously or in the order it is received into the language used by the student at the educational program distribution company's server 8 and distribute through the internet 9 to the students personal computer 7a-1~7a-N.

On the other hand, as shown in FIG. 3, when student 3b is to receive instruction from a specialized instructor located at a remote location, the data of the expanded viewpoint image obtained from the two dimensional or three dimensional CCD cameras 1c of the digital magnifying device shown in FIG. 1 worn by the student 1b, with vital sign data B or image data B obtained from the precision technique facility/equipment/environment monitoring device superimposed on the above viewpoint image data, and the data of the questions C from the student inputted through the microphone 1b, and modification input device 4 inputs the data into the personal computer 6b, and through the internet 9, the data is sent to the technical guidance educational distribution system distribution company's server 8 from the personal computer 6b.

When the language used by the specialized instructor and the student 3b is different for the above referenced data, the data is to be simultaneously or in the order it is received, translated to the language used by the instructor at the educational program distribution company's server 8 and then sent to the instructor. Here, from the educational program distribution company's server 8, through the internet 9, the data is sent to the instructor's personal computer 7b-1~7b-N or if the program involves technical instructions of several different fields, the data is sent to several instructors' personal computers 7b-1~7b-N.

The specialized instructor observing the expanded viewpoint image data A and the vital sign data B or the image data B from the precision technique facility/equipment/environment monitoring device superimposed on the above viewpoint image data displayed on their personal computer 7b-1~7b-N, and using the persona computer 7b-1~7b-N, and the mouse 11 to provide direct instruction on the image and/or by microphone 13, provide oral instruction and input, and these inputted information are forwarded in the reverse direction through the internet 9 to the technical guidance educational distribution system distribution company's server 8, and further through the internet 9 sent to the student.

When the language used by the specialized instructor and the student is different, the data may be translated simultaneously or in the order received into the language used by the student at the educational program distribution company's server 8, and directly displayed on the eye glass type LCD monitor equipped with CCD cameras 1d shown in FIG. 1 as cursor information and/or as voice instructional information through the earphone 1a. By allowing two way communication for the contracting student, educational instructional service for practical skills is established/enabled.

Also, the personal computer 6 and the personal computer 7, both connected to the internet 9, as mentioned connected to the internet 9 and of course capable of accessing the home page of the educational program distribution company's server 8.

By the internet connection, when a student purchases a program through the educational program distribution company's home page, the home page of the educational program distribution company could post information for each program offered, such as instructor's background, description of the technical skill, area of expertise, language used, length of instruction, fee, and other information which may be found in a traditional advertisement and in addition a popularity of the program may also be updated/displayed on the web site on a real time basis, and also allow students to read the comments by other students who have taken the program by the same instructor, it will allow the students to make decision based not only on advertisement placed by the instructor and/or on subjective view of the students acquaintances who has take the program. Also, when the students applies for a program, it is also possible to settle the payment for a program on the educational program distribution company's home page.

In addition, the instructor of an educational program may by utilizing the educational program distribution company's home page, place advertisement of the program and to receive and process application from students, and to settle payment and receipt of instruction fees.

On the other hand when a student purchases a individual technical education/guidance education program which there are more than one instructors providing instructions in each instructors' area of expertise, student can see the information such as technical expertise of each instructor, type of technical instructions, language used, and length of instruction and instruction fees on the education program distribution company's internet home page web site and make a decision, not based on an biased advertisement placed by the instructor or on a subjective view/opinion of an acquaintance of the student who has taken the program from the instructor, but to make an informed decision and even request a particular instructor for a program.

In addition, the instruction fee is posted on the education program distribution company's internet home page web site eliminating the need to individually negotiate a fee with the instructor, and the education program distribution company forms a team of expert instructor to provide a education program of very high technical level. Also, the student through the internet home page web site of the educational program distribution company, can settle payments of instructional fees.

In addition, the instructor based on the time unit or the unit for the type of the technical instruction provided, automatically receive the proper instruction fees based on the number of students taking the program and number of instructors involved in the program, and the instructor is also relieved from the administrative procedure of accounting/collecting and dividing the fees (if multiple instructors) according to the involvement.

It should further noted that it is also possible to make changes (alterations) to the eye glass type monitor worn on the head of the technician, the digital magnifying mirror placed on the front portion of the monitor with two zoom lens equipped auto focus three dimensional CCD cameras placed in front of the pupils of the person performing the work towards the viewpoint of the person performing the work, earphone, and voice microphone, and the communication and/or distribution network utilizing the internet, so long as it is within the general scope of the invention.

Figure 4:
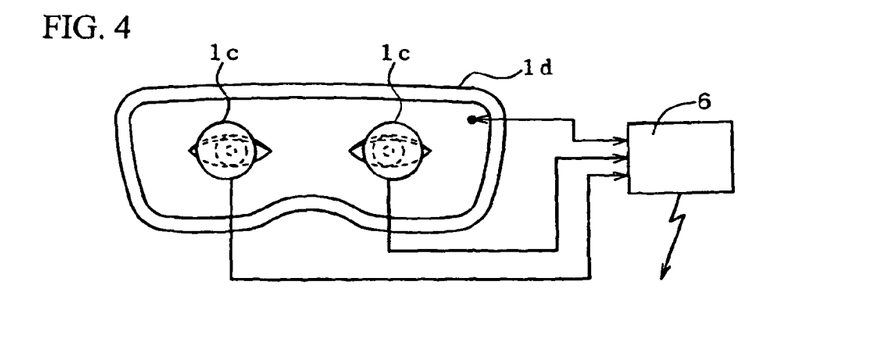
FIG. 4 is a schematic illustration of eye glass type monitor and three dimensional CCD cameras suitable for being used in this invention.

There is provided the detailed description of the eye glass type monitor and CCD cameras. As shown in FIG. 4, the monitor 1d is placed to cover and expand around both the left and right eyes of the instructor, and can be worn in a similar fashion as an eye glass or a sun glass. Also the three dimensional CCD cameras 1c, as worn over the head (face), approximately corresponds the center of the right and left pupils, and arranged to in one piece with the monitor 1d. The two CCD cameras combined may be considered to be a three dimensional CCD cameras or each CCD cameras individually may also be considered to be a three dimensional cameras.

Figure 5:
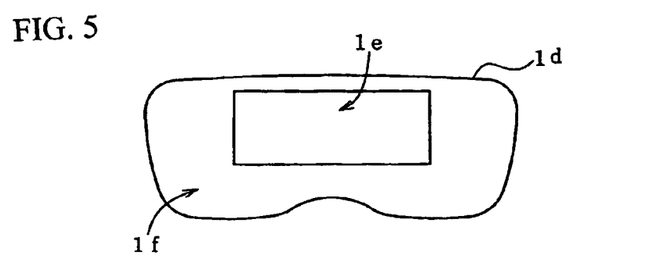
FIG. 5 is an illustration showing one example of how the display section of the monitor may look on the monitor the referred in FIG. 4.

Each cameras 1c, is desirable to be equipped with zoom lens and to be a auto focus CCD cameras. By using such type of cameras, which is automatically programmed to automatically focus on the proper target, regardless of the distance between the head of the person performing the work where the cameras is located and the location where the work/surgery is performed and also regardless of the magnification level. The data inputted from such cameras is processed by the image processing device within the personal computer 6, divided into separate images, and as shown in FIG. 5, the magnified section of the image is displayed in the center display section 1e of the monitor and non-magnified section of the image is displayed in certain multiple of magnification or at a lower magnification in the remaining display section if of the monitor 1d. Such combined processed image may be displayed on the monitor 1d of the technician and the same image also displayed on the display monitor of the device where the image is distributed (sent).

Figure 6:
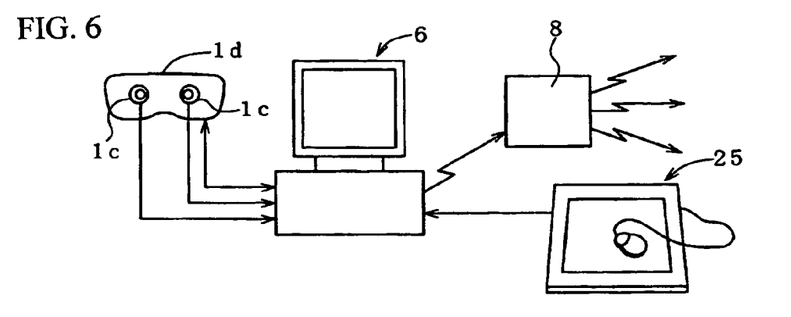
FIG. 6 is a block diagram of a system comprising the eye glass type monitor, CCD cameras and input assistance such as arrows and pointers for additional information.

When using cursor pointer, lines, and/or arrows to add instruction or other additional information to the image captured by the above referenced cameras 1c, as shown in FIG. 6, by using an additional information input device attached to the computer 6, for example such as a pen tablet input or liquid crystal tablet, and the additional information inputted through the device and the image from the cameras 1c, using the above referenced image processing device, are combined and composed into an image and sent to the monitor worn by the technician performing the work and to other devices (personal computers). It is not easily possible for the person actually performing the work to input additional information to the live image distributed, the input process will be performed by another person. If the input is to be performed by the technician performing the work, the image captured by cameras 1c may be first saved in the memory device (internal memory device within the computer 6, or an outside device attached as outside memory device) and the technician is to input additional information later, then the images are to combined/composed and distributed.

Figure 7:
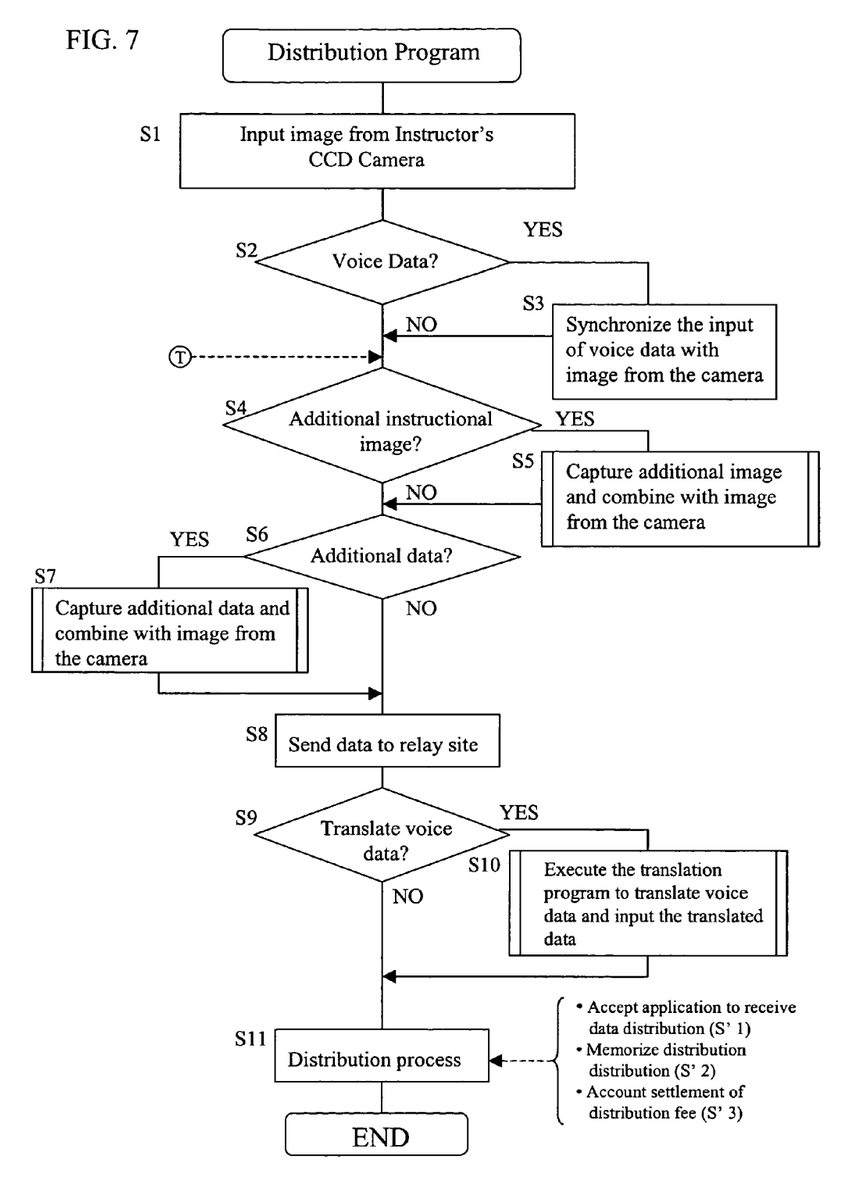
FIG. 7 is a flow chart of how the data of the image from the eye glass type monitor is distributed to the devices in remote location.

FIG. 7 is a flow chart showing the overall process of distribution system. At step S1 (S1), the image captured by the CCD cameras 1c is entered/inputted into the computer 6. If there is additional voice information from the microphone of the technician, through S2 and at S3 the voice data and the cameras image is to be combined so the data are synchronized as inputted into the computer. Additionally, any additional information such as pointer, line, explanatory language and other information, through S4 and at S5, the additional information/data inputted separately is captured, and combined/composed with the cameras image. Further, at S6, decisions are made to whether add such information like the patient's vital signs and/or the RPM of the surgical tool and other information surrounding the technical environment, and if the decision is made to add such information, the information is inputted at S7 and combined/composed with the cameras image. Additional information such as the information of the technical environment may be displayed for example on the area other than the center area of the monitor's 1d, such as the surrounding display area 1f.

Above stated information, such as the image from the cameras and if necessary combined/composed with voice data and/or other additional information, is first sent to the relay site S8 (educational program distribution company's server), and from there, through communication method such as the internet, distributed to several end devices. Prior to the distribution, if it is decided that translate the voice data, the voice data at S10 undergoes the translation routine, and it is translated simultaneously or if it is to be distributed at a later time, translated as a preparation for a later distribution, and the translated data is captured. Also, the translation is not limited to voice data, and for example additional instructional comments in writing and/or the surrounding technical environmental information in writing, may also be translated into specified language, and to capture such translation data. Also the translation step may be performed not only at the distribution company's server but may also be performed before at section T (before S4), and send the translated data to the distribution company's server.

Either way, at S11, through the internet or other communication method from the distribution company's server 8, data such as the image captured by the CCD cameras of the technician and other additional data such as pointer and surgical equipment's basic set up data (such as the RPM of the equipment) and other technical environmental data, combined/composed, and in addition as required, voice data from the technician's microphone, are sent out to several monitor device. Also the same information/data referenced above are sent to the monitor 1d of the technician, and is possible to set up the program so the technician and the persons receiving the transferred data, are both seeing the same combined image.

As a prerequisite before the distribution process S11, by utilizing such communication method as the internet, the processing the application for the program is performed (S'1), and the distribution destination receiving the application is memorized, and settlement for distribution, instruction is performed (S'3). The processing of application to the program is triggered when a person accesses the distribution company's server 8, which the program set up in the distribution company's server 8 starts to run, triggering the application processing process. The actual settlement of the distribution fee may be done after the completion of distribution processing S11.

Figure 8:
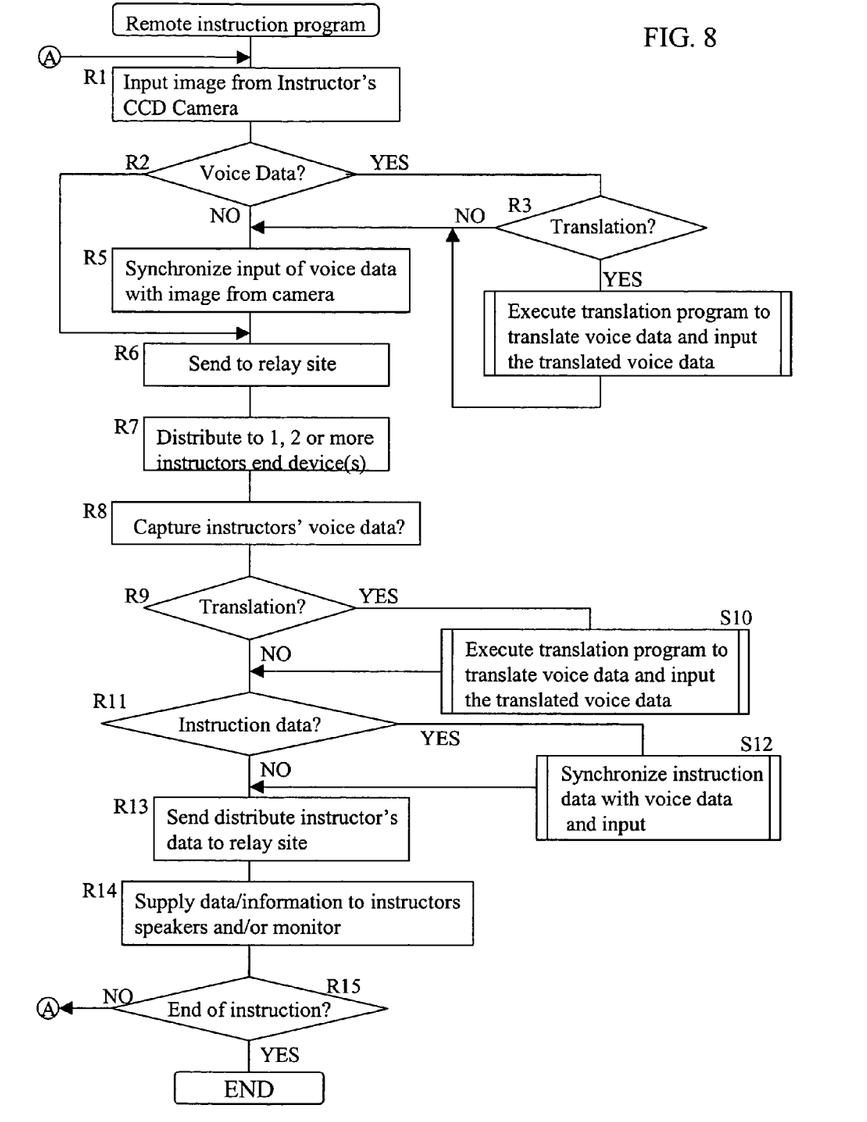
FIG. 8 is a flow chart of how the data of the image from the eye glass type monitor worn by the technician is distributed to the devices in remote location and how instructional information/data is sent out to the technician.

FIG. 8, an ideal example, as shown in FIG. 7 which the image data from the cameras of the technician is received by the instructor at a remote location, and by using two way communication method such as the internet, the image data and/or the voice data are sent to the instructor who the technician desires to receive instruction, is a flow chart showing of such system where two way communication is used in such manner. Through step R1~R7, the range of vision of the technician who is to receive the instruction from the instructor is projected on the monitor of the instructor (one-way communication). If there is voice data from the technician, translation would be performed on the data if necessary, and also transferred to the instructor.

The instructor receiving these data, by utilizing their device (computer?) may enter instructional information (for example voice instructional data and other), and at R8 the voice data of the instructor is entered into the device, and if translation is necessary, the data is translated at R10 after passing through R9, and if there is additional information other than voice data, such as pointers (cursor), line, words and other information, are to be added to the image data sent at R7, it will be captured at R12 after passing through R11. In order to allow the data written into the delivered image data to be projected on the technician's monitor as it is written, the data written in is connected to the information coordinate data of the technician's monitor and captured.

Then at R13, such data like the one referenced above is sent from the instructor to the relay site (distribution company's server), and from here, passes through the device of the technician and at R14 outputted through the speaker of the technician (generally through the earphone or other outputting device worn by the technician) and or the eye glass type monitor worn by the technician, and the information from the instructor at a remote location through pointers, voice or other method on the instructional image data, allows the technician to work and receive instructions as though the instructor is giving instruction at the site or right next to the technician. Until the instruction ends at s15, the instruction continues through two way communications by returning to R1 and to later stages. It should be noted that the information may be sent directly to the device of the technician without passing through or being sent to a relay site. In such situation, R13 is eliminated. This situation is same for S8 in FIG. 7, as the data from the technician may be sent directly to the instructor or to numerous devices without passing through or sent to a relay site.

Figure 9:
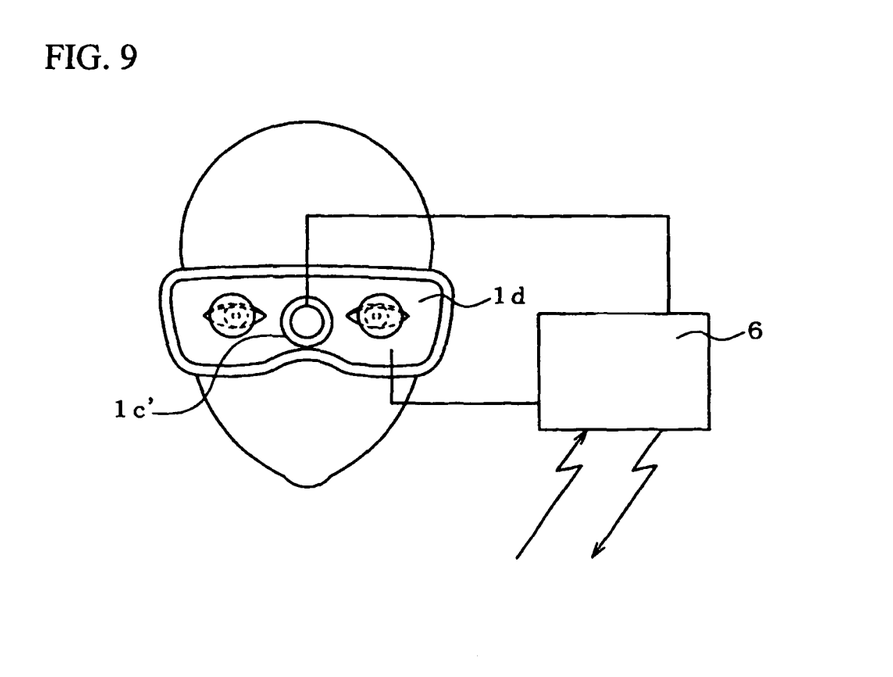
FIG. 9 is a schematic diagram showing an alternative example of this invention when two dimensional CCD cameras is used.
Figure 10:
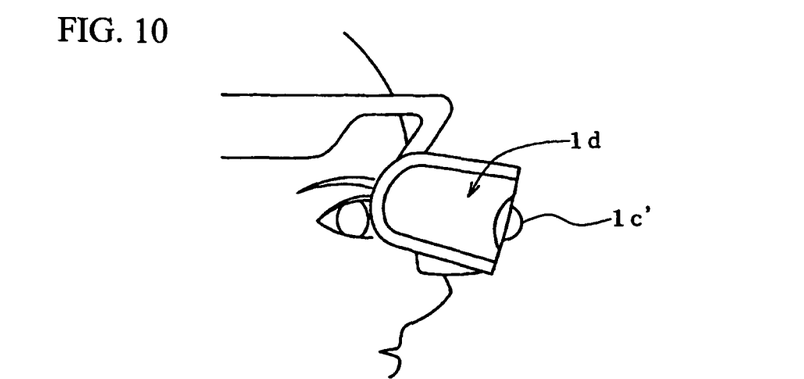
FIG. 10 is a side view of a head mount used in the example of FIG. 9.

In the above explanation, the technician or the person performing the precision work utilized the three dimensional CCD cameras equipped in the eye glass type monitor but as shown in FIG. 9 and FIG. 10, a monitor 1d may be placed together with one two dimensional CCD camera placed in the center between the right and left pupil of the technician, and substitute the image captured by this cameras instead of the image from the three dimensional CCD image.

It should also be noted that FIG. 10 is the side view figure that corresponds to FIG. 4. The above description premised on utilizing internet but this invention is not limited on utilizing the internet, but such communication network such as a closed end network of intranet, or other dedicated communication network or communication circuit may be used. In additional, as a communication method, a communication method utilizing satellite may also be selected.

The foregoing explanation is based on utilizing two zoom lens equipped auto focus CCD cameras but cameras without a zoom lens, or a camera that is not a CCD camera, and other image capturing device may be used.

On the image which is the same image on the above referenced eye glass type monitor, which the instructor or another person by using cursor pointer, lines, arrow and other method to write in or to add instructional explanation or pointer information, the image data with such additional information is sent via internet or other communication network, the image may be paused and used as a still image, and writing of the additional information such as pointers, may be written in while the image is paused, and the paused image with the additional information written in may be composed with the actual image and send to several devices to the students receiving instruction. In the other hand, if the technician is to receive instruction from an instructor at a remote location, the instructor may pause the image sent to the instructor and, write the additional information such as pointers onto the paused image, and compose the image with the actual image and send to the technician's monitor. Such writing in of additional information may also be done on non still image, and although this feature of writing in on still image is not to eliminate the feature of writing into live/non-still image, it is possible that the technician may move while writing in additional information onto a live image, which may cause the pointer or other additional written in instruction to appear at a location different from the place where the actual write in information was intended. In such case, it is very effective to pause the image and then again return to live image there after. It should be noted that additional information written in, such as pointer information, in situation where the instructor is actually performing the work (technician is the instructor), a third party adding live commentary to the instruction, or the person in charge of providing instruction at the education system distribution company where the server is located, to provide/enter the additional information would be the more common method of inputting the instruction additional information to the image. Also, in some situation, the instructor/technician may actually stop the work, and input the additional information, such as instructional pointers, using an inputting device located nearby. The technology behind pausing an image, adding additional information to the paused image, and then return again to the moving image is a known technology, therefore detailed explanation of this technology will be avoided here, but in general a moment of an image from the CCD cameras' or other device's image is stored in memory of the cameras, while reading this memory, the information inputted using such input device as pointer (applicable to both moving and still image) and its image is captured, then a layering process, composition of the images using memory, or another known method of composing images is used to compose the two images.

As explained above, this invention is a remote internet technical instructional/educational distribution system utilizing the perception of the technician, and the instructional system utilizes communication network, such as the internet and distributes live or recorded medical surgery and/or highly precision oriented technical work's instructional program which are performed under the direct observation of the technician, or a instructional program for medical surgery or highly precision oriented technical work performed by the student, (a person without the necessary expertise is perceived as a robot with artificial intelligence and from a remote location looking at the same the view point perception of the person, and from the information received, control the movements of the person using voice and perceptional instruction), which this invention allows the reduction of cost, time and distance for such program, and in addition provides a method of recruiting students and instructor, a method for evaluating the technical aspect of the instructor, and a method for paying/collecting instruction fees and settling the accounts through the internet.

The invention claimed is:

1. A head mount to be placed over a head of an instructor for use with a technique training distribution system for utilizing the internet for distributing training programs for education of medical operation or other precision techniques through the internet as communication means, said head mount comprising:
    two zoom lens equipped auto-focus CCD cameras to be placed on the front of the head mount, each CCD camera directly in front of a respective pupil of the instructor's eyes, an optical axis of each CCD camera in line with the respective pupil for capturing input image from each CCD camera, wherein said input image from the two CCD cameras to be combined into two dimensional or three dimensional input image;
    an LCD display to be placed on the front of the head mount in line with the vision of the instructor for projecting and displaying the two dimensional or three dimensional input image, and
    means for receiving information collected from the surrounding environment or from equipment, said LCD display displaying not only the two dimensional or three dimensional input image but also the information collected from the surrounding environment or from equipment,
    wherein the two zoom lens equipped auto-focus CCD cameras and the LCD display and the receiving means are assembled as one piece with said head mount so that the two zoom lens of the instructor to enhance operability of image capturing and image and information monitoring performances of the head mount.

2. The head mount according to claim 1 additionally comprising:
    an earphone worn by the instructor to receive voice data which is forward to the earphone worn by the instructor; and
    a microphone worn by the instructor to capture and send voice data of the instructor;
    means for superimposing the collected information onto the image from the cameras worn by the instructor; and
    means for displaying the combined information on the eyeglass type monitor worn by the instructor, and to forward the combined image to an education program distribution server.

3. The head mount according to claim 1 additionally comprising:
    a microphone worn by an instructor; and
    means for allowing the distribution of the voice data along with the image to an educational program distributing server.

4. The head mount according claim 1 additionally comprising:
    means for translating voice data of the instructor in the order received or simultaneously at an education program distribution server to the language used by the subscribers.

5. The head mount according claim 1, wherein each CCD camera corresponds to each pupil of the instructor's eyes.

6. A head mount to be placed over a head of an instructor for use with a technique training distribution system for utilizing the internet for distributing training programs for education of medical operation or other precision techniques through the internet as communication means, said head mount comprising:
    two zoom lens equipped auto-focus CCD cameras to be placed on the front of the head mount, each CCD camera directly in front of a respective pupil of the instructor's eyes, an optical axis of each CCD camera in line with the respective pupil for capturing input image from each CCD camera, wherein said input image from the two CCD cameras to be combined into two dimensional or three dimensional input image;

an LCD display to be placed on the front of the head mount in line with the vision of the instructor for projecting and displaying the two dimensional or three dimensional input image, said LCD display having a center display section for displaying a magnified section of the two dimensional or three dimensional input image and another display section for displaying a non-magnified section of the two dimensional or three dimensional input image, means for receiving information collected from the surrounding environment or from equipment, said LCD display displaying not only the two dimensional or three dimensional input image but also the information collected from the surrounding environment or from equipment, wherein the two zoom lens equipped auto-focus CCD cameras and the LCD display and the receiving means are assembled as one piece with said head mount so that the two zoom lens equipped auto-focus CCD cameras and the LCD display are both aligned with the vision of the instructor to enhance operability of image capturing and monitoring performance of the head mount.

* * * * *